(12) United States Patent
Hsu

(10) Patent No.: US 9,433,694 B1
(45) Date of Patent: Sep. 6, 2016

(54) TOOTHBRUSH STERILIZATION CABINET

(71) Applicant: Chen-Wei Hsu, New Taipei (TW)

(72) Inventor: Chen-Wei Hsu, New Taipei (TW)

( * ) Notice: Subject to any disclaimer, the term of this patent is extended or adjusted under 35 U.S.C. 154(b) by 0 days.

(21) Appl. No.: 14/751,577

(22) Filed: Jun. 26, 2015

(51) Int. Cl.
*A61L 2/10* (2006.01)

(52) U.S. Cl.
CPC ....................................... *A61L 2/10* (2013.01)

(58) Field of Classification Search
USPC .............. 250/455.11, 454.11; 422/22, 24, 26
See application file for complete search history.

(56) References Cited

U.S. PATENT DOCUMENTS

| | | | | |
|---|---|---|---|---|
| 2,579,242 A | * | 12/1951 | Pask | ......................... A61L 2/10 250/455.11 |
| 4,740,706 A | * | 4/1988 | Murdock, III | ............ A61L 2/10 250/455.11 |
| 4,845,859 A | * | 7/1989 | Evans | ...................... A47K 1/09 219/242 |

* cited by examiner

*Primary Examiner* — Kiet T Nguyen
(74) *Attorney, Agent, or Firm* — Rosenberg, Klein & Lee

(57) ABSTRACT

A toothbrush sterilization cabinet includes a housing, a sliding plate movable in and out of the housing, a rack rotatably mounted at the sliding plate for holding toothbrushes and/or razors, a control circuit, a hot air generator consisting of an electrical heating element and an electrical fan, an UV germicidal lamp and an ozone generator for generating hot air, UV light or ozone, and a tact switch for driving the control circuit to turn on the hot air generator, the UV germicidal lamp and/or the ozone generator for a predetermined length of time.

10 Claims, 6 Drawing Sheets

TOOTHBRUSH STERILIZATION CABINET

BACKGROUND OF THE INVENTION

1. Field of the Invention

The present invention relates to bathroom cabinets and more particularly, to a toothbrush sterilization cabinet for use in a bathroom for holding toothbrushes and razors and drying and sterilizing storage toothbrushes and razors.

2. Description of the Related Art

Toothbrushes can become contaminated with oral microbial organisms whenever they are placed in the mouth. It is important to keep a toothbrush clean and dry, and a toothbrush cap helps with this. There are commercial apparatuses for drying or sterilizing toothbrushes, preventing toothbrush bacteria growth. However, these apparatuses simply provide one single function, i.e., an apparatus for drying (or sterilizing) toothbrushes is not practical for sterilizing (or drying) toothbrush. It is expensive to prepare many different apparatuses having different functions. Further, these apparatuses do not facilitate convenient access to storage toothbrushes.

SUMMARY OF THE INVENTION

The present invention has been accomplished under the circumstances in view. It is one object of the present invention to provide a toothbrush sterilization cabinet, which is practical for holding toothbrushes and razors and operable to dry and sterilize storage toothbrushes and razors.

To achieve this and other objects of the present invention, a toothbrush sterilization cabinet comprises a housing, two sliding rails bilaterally symmetrically mounted at a bottom side inside the housing, a sliding plate coupled to the sliding rails and movable along the sliding rails in and out of the housing, a door panel hinged to the housing and biasable between an open position to open a front open side of the housing and a close position to close the front open side of the housing, a connection member connected between the door panel and the sliding plate for enabling the sliding plate to be moved with the door panel in and out of the housing, a rack detachably and rotatably mounted at the sliding plate for holding toothbrushes and/or razor, a control circuit mounted inside the housing, a hot air generator mounted inside the housing and controllable by the control circuit to generate hot air, an UV germicidal lamp mounted inside the housing and controllable by the control circuit to generate UV light, a tact switch mounted at a front side of the housing and switchable to drive the control circuit to turn on the hot air generator and UV germicidal lamp for a predetermined length of time, a power jack mounted outside the housing and electrically connected to the control circuit, and a power adapter adapted for electrically connecting the power jack to an external power source to provide electricity to the control circuit, the hot air generator and the UV germicidal lamp.

DETAILED DESCRIPTION OF THE PREFERRED EMBODIMENT

Figure 1:
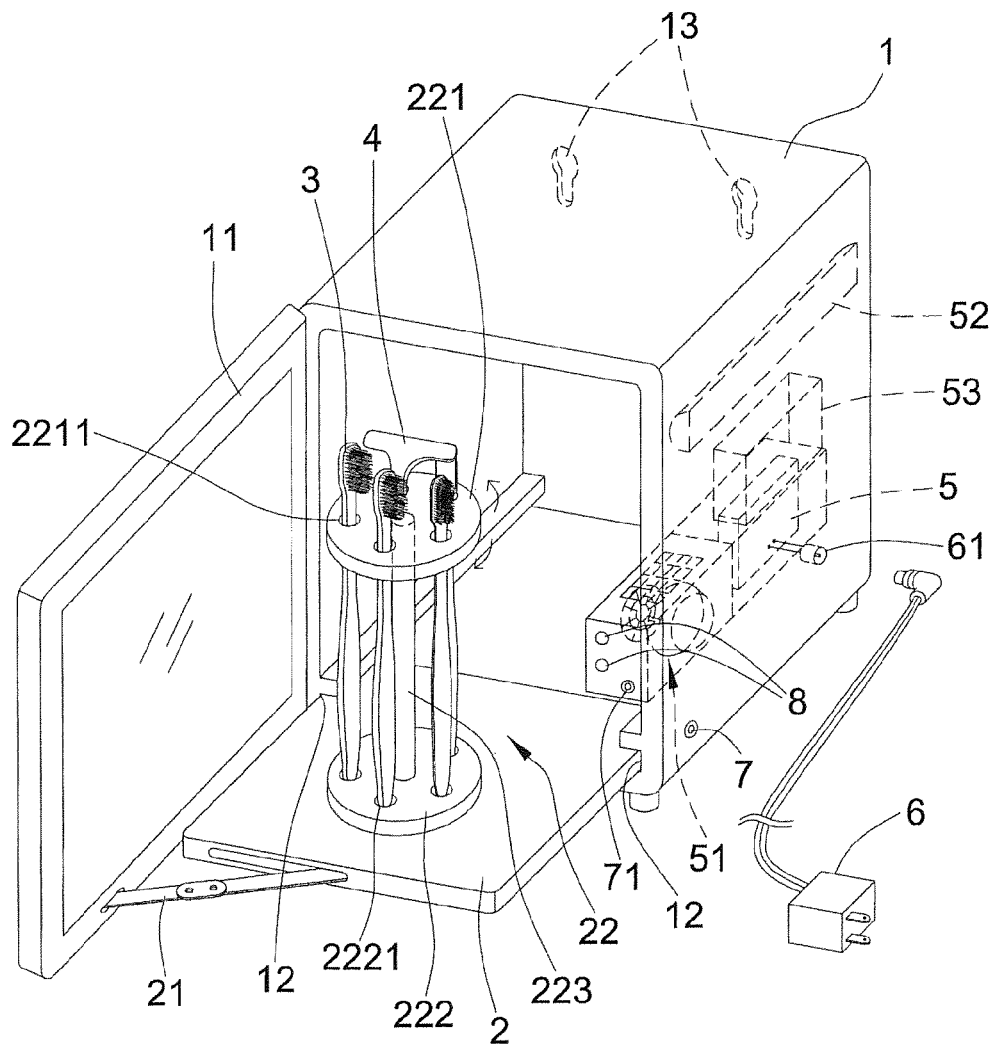
FIG. 1 is a perspective view of a toothbrush sterilization cabinet in accordance with the present invention.
Figure 2:
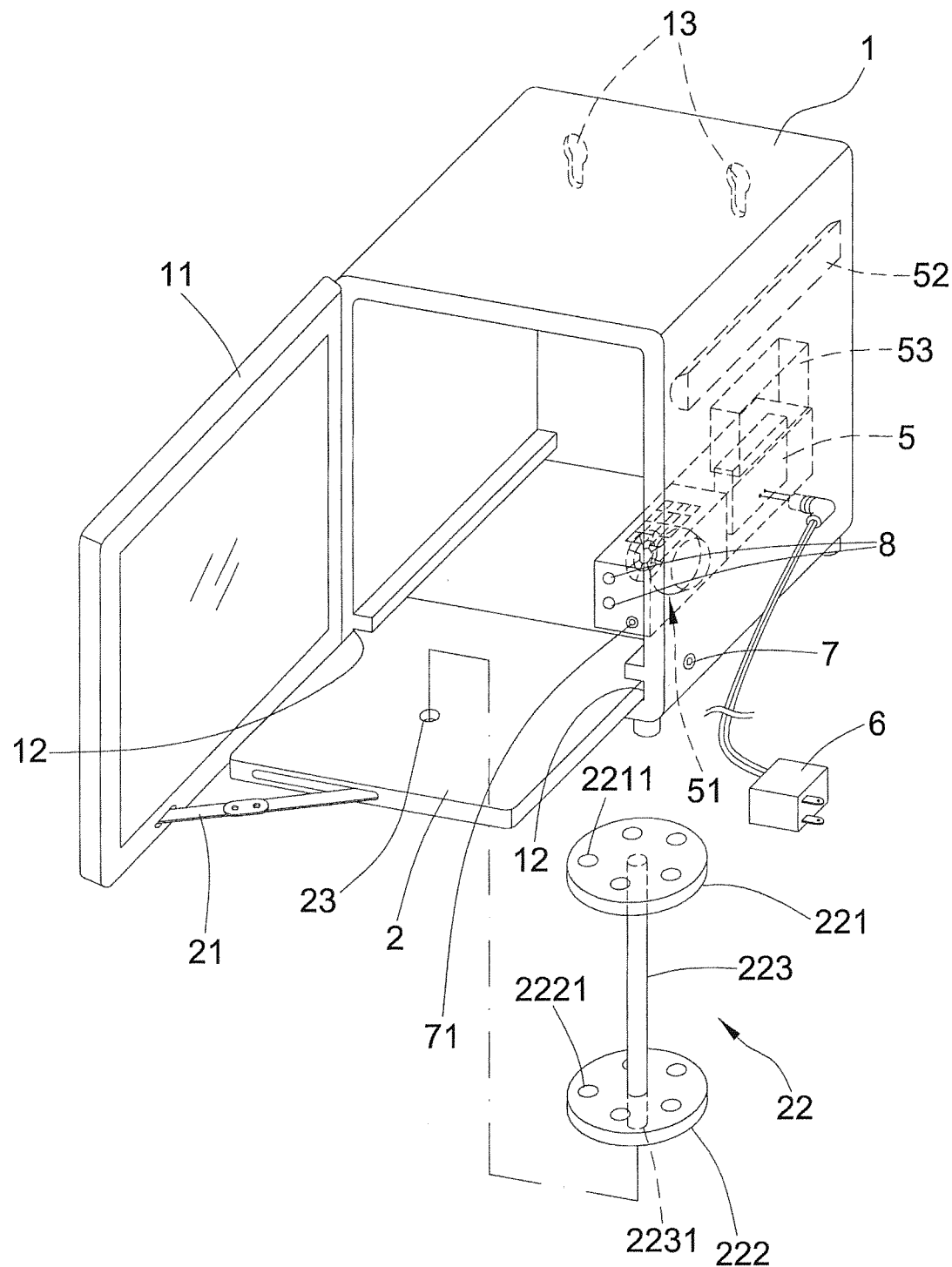
FIG. 2 is an exploded view of the toothbrush sterilization cabinet in accordance with the present invention.
Figure 3:
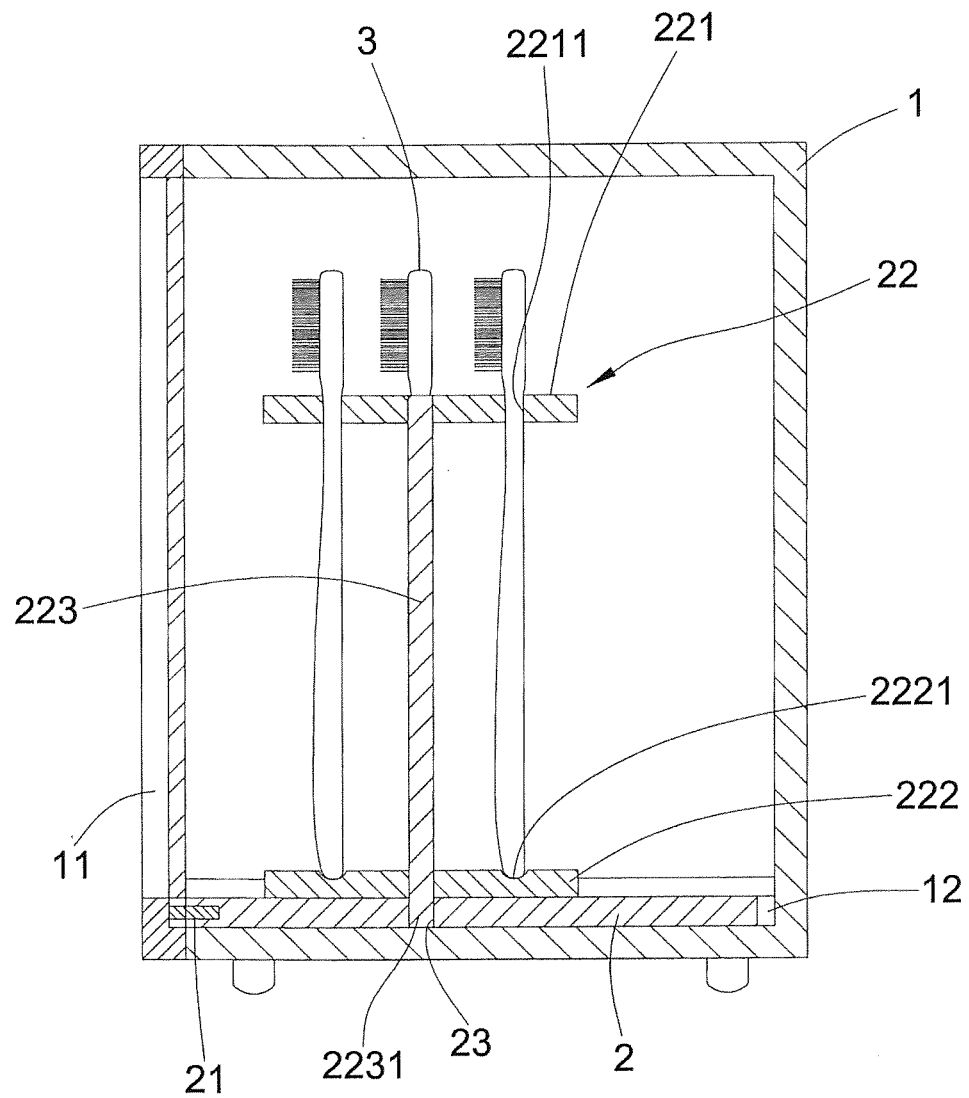
FIG. 3 is a sectional side view of the toothbrush sterilization cabinet in accordance with the present invention, illustrating the door panel in the close position.
Figure 4:
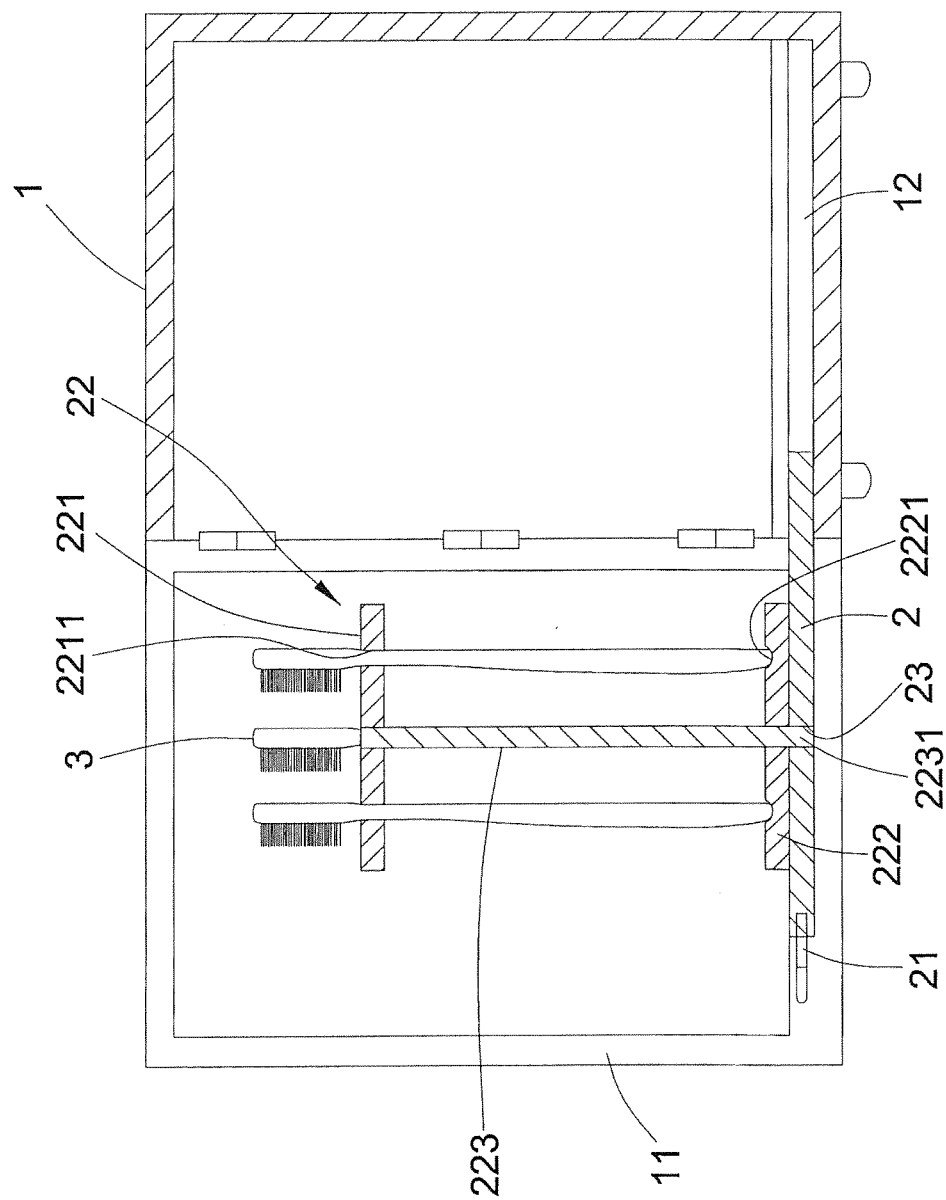
FIG. 4 corresponds to FIG. 3, illustrating the door panel in the open position.
Figure 5:
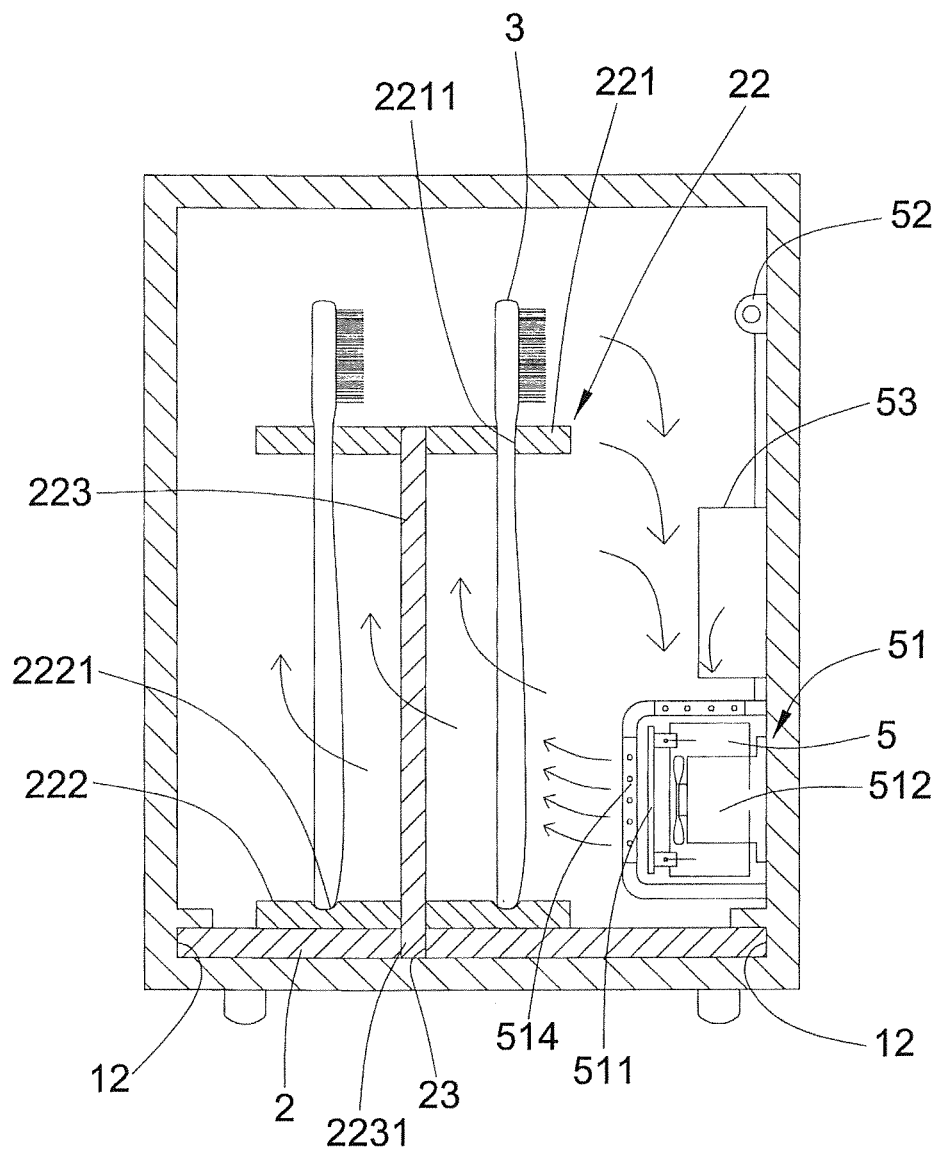
FIG. 5 is a schematic sectional front view of the present invention, illustrating an operation status of the toothbrush sterilization cabinet.

Referring to FIGS. 1-4, a toothbrush sterilization cabinet in accordance with the present invention is shown. The toothbrush sterilization cabinet generally comprises a housing (1), two sliding rails (12) bilaterally symmetrically mounted on a bottom side inside the housing (1), a sliding plate (2) coupled to and movable along the sliding rails (12), a door panel (11) hinged to the housing (1) and biasable to close/open a front open side of the housing (1), a connection member (21) coupled between the door panel (11) and the sliding plate (2) for enabling the sliding plate (2) to be moved in and out of the housing (1) when the user closes or opens the door panel (11), and a rack (22) mounted at the sliding plate (2) for holding toothbrushes (3) and/or razors (4). The rack (22) comprises an upper rack plate (221), a lower rack plate (222), and a post (223) inserted through the upper rack plate (221) and the lower rack plate (222) at the center to hold the upper rack plate (221) and the lower rack plate (222) at different elevations. The upper rack plate (221) has a plurality of insertion holes (2211) equiangularly spaced around the post (223) for the insertion of toothbrushes (3) and/or razors (4) individually. The lower rack plate (222) has a plurality of grooves (2221) corresponding to the insertion holes (2211) of the upper rack plate (221) for the positioning of the bottom ends of the toothbrushes (3) or razors (4) that are respectively inserted through the insertion holes (2211) of the upper rack plate (221). The post (223) has the bottom end (2231) thereof detachably coupled to a mounting hole (23) at the sliding plate (2) for allowing the rack (22) to be rotated relative to the sliding plate (2) or detached from the sliding plate (2) for a replacement. When the user opens or closes the door panel (11), the connection member (21) is forced to move the sliding plate (2) and the rack (22) out of or into the housing (1) so that the user can access to the storage toothbrushes (3) and/or razors (4). The toothbrush sterilization cabinet further comprises a control circuit (5) mounted in the housing (1), and a hot air generator (51) controllable by the control circuit (5). The hot air generator (51) comprises an electrical heating element (511), an electrical fan (512), an air inlet (513), and an air outlet (514) (see FIG. 5). The toothbrush sterilization cabinet further comprises an UV germicidal lamp (52) mounted inside the housing (1) at an elevation corresponding to the storage toothbrushes (3) and/or razors (4) and controllable by the control circuit (5), an ozone generator (53) mounted in the housing (1) above the control circuit (5) and controllable by the control circuit (5), a tact switch (7) mounted in an outside wall of the housing (1) and switchable to drive the control circuit (5) in turning on the electrical heating element (511) and electrical fan (512) of the hot air generator (51) and the UV germicidal lamp (52) or ozone generator (53) to dry the storage toothbrushes (3) and/or razors (4) and to generate ozone for sterilization, and a power jack (61) mounted near a rear side of the housing (1) for connection to a city power supply outlet by means of a power adapter (6) for providing the necessary working electricity to the control circuit (5), the hot air generator (51), the UV germicidal lamp (52) and the ozone generator (53). Further, the housing (1) provides at least one, for example, two hanging holes (13) at the rear side thereof for hanging from a high place.

Further, another tact switch (71) is provided at a front side of the housing (1) and operable to turn on/off the UV germicidal lamp (52). Each time the user closes the door panel (11), the tact switch (71) is switched on by the door panel (11) to drive the control circuit (5) to turn on the UV germicidal lamp (52) for sterilization. The control circuit (5) is a programmable circuit programmed to turn off the UV germicidal lamp (52) a set time after the UV germicidal lamp (52) has been turned on.

Thus, after the control circuit (5) turned on the hot air generator (51) and the UV germicidal lamp (52), the control circuit (5) will automatically turn off the hot air generator (51) and the UV germicidal lamp (52) when the set time is up. Further, indicator lights (8) are mounted at the front side of the housing (1) adjacent to the tact switch (71) for indicating the operation status of the hot air generator (51) and the UV germicidal lamp (52).

Figure 6:
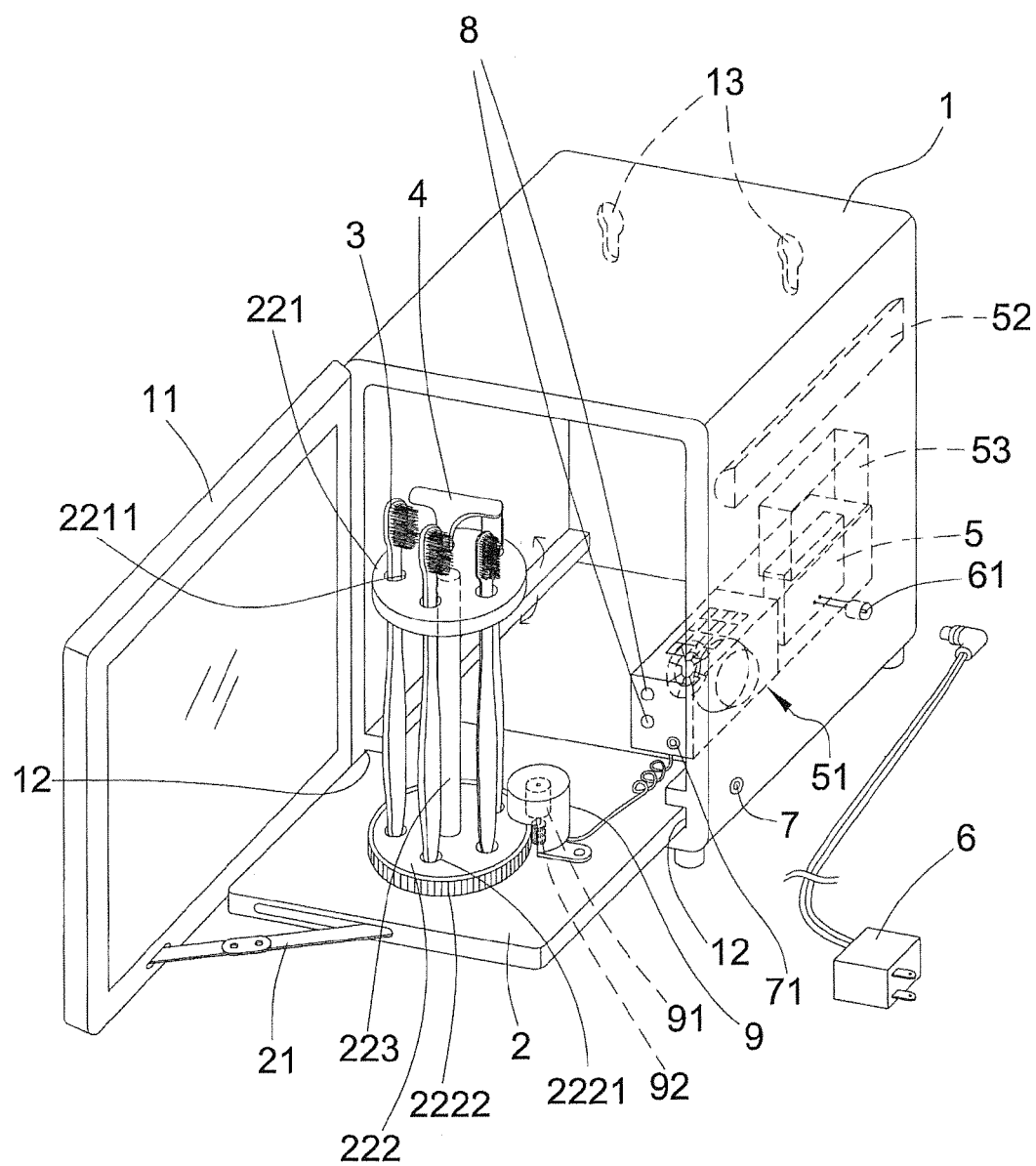
FIG. 6 is a perspective view of an alternate form of the toothbrush sterilization cabinet in accordance with the present invention, illustrating a motor fixedly mounted at the sliding plate adjacent to the lower rack plate of the rack and a pinion meshed with the gearwheel of the lower rack plate and coupled to the output shaft of the motor.

Further, as shown in FIG. 6, the lower rack plate (222) comprises a gearwheel (2222) integrated therein. Further, a motor (91) is mounted in a motor housing (9) at the sliding plate (2). After the door panel (11) has been closed, the user can press the tact switch (7) to drive the control circuit (5) to start up the motor (91), causing a pinion (92) (that is mounted on the output shaft of the motor) to rotate the gearwheel (2222) of the lower rack plate (222), and thus, the rack (22) is rotated in the housing (1) for enabling the storage toothbrushes (3) and/or razors (4) to be well dried and sterilized (see FIG. 6).

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A toothbrush sterilization cabinet, comprising:
a housing;
two sliding rails bilaterally symmetrically mounted at a bottom side inside said housing;
a sliding plate coupled to said sliding rails and movable along said sliding rails in and out of said housing;
a door panel hinged to said housing and biasable between an open position to open a front open side of said housing and a close position to close said front open side of said housing;
a connection member connected between said door panel and said sliding plate for enabling said sliding plate to be moved with said door panel in and out of said housing;
a rack detachably and rotatably mounted at said sliding plate for holding toothbrushes and/or razors;
a control circuit mounted inside said housing;
a hot air generator mounted inside said housing and controllable by said control circuit to generate hot air;
an UV germicidal lamp mounted inside said housing and controllable by said control circuit to generate UV light;
a tact switch mounted at a front side of said housing and switchable to drive said control circuit to turn on said hot air generator and UV germicidal lamp for a predetermined length of time;
a power jack mounted outside said housing and electrically connected to said control circuit; and
a power adapter adapted for electrically connecting said power jack to an external power source to provide electricity to said control circuit, said hot air generator and said UV germicidal lamp.

2. The toothbrush sterilization cabinet as claimed in claim 1, further comprising an ozone generator mounted in said housing above said control circuit and electrically connected to said control circuit and controllable by said control circuit to generate ozone for a set length of time after said the user closes said door panel and switches on said tact switch.

3. The toothbrush sterilization cabinet as claimed in claim 1, wherein said rack comprises an upper rack plate, a lower rack plate and a post holding said upper rack plate and said lower rack plate at different elevations, said upper rack plate comprising a plurality of insertion holes equiangularly spaced around said post for the insertion of toothbrushes and/or razors individually, said lower rack plate comprising a plurality of grooves corresponding to said insertion holes of said upper rack plate for the positioning of respective bottom ends of toothbrushes and/or razors that are respectively inserted through said insertion holes.

4. The toothbrush sterilization cabinet as claimed in claim 1, wherein said hot air generator comprises an electrical heating element controllable by said control circuit to generate heat, an electrical fan controllable by said control circuit to induce currents of air toward said electrical heating element, an air inlet for letting fresh air in, and an air outlet for letting hot air out.

5. The toothbrush sterilization cabinet as claimed in claim 1, wherein said control circuit is a programmable circuit programmed to turn off said hot air generator and said UV germicidal lamp a set time after said hot air generator and said UV germicidal lamp have been turned on.

6. The toothbrush sterilization cabinet as claimed in claim 1, further comprising a plurality of indicator lights electrically connected to said control circuit and adapted for indicating the operation status of said hot air generator and said UV germicidal lamp.

7. The toothbrush sterilization cabinet as claimed in claim 1, further comprising a second tact switch mounted at a front side of said housing and switchable by said door panel to turn on said UV germicidal lamp for a predetermined length of time subject to the control of said control circuit each time said door panel is closed on said housing.

8. A toothbrush sterilization cabinet, comprising:
a housing;
two sliding rails bilaterally symmetrically mounted at a bottom side inside said housing;
a sliding plate coupled to said sliding rails and movable along said sliding rails in and out of said housing;
a door panel hinged to said housing and biasable between an open position to open a front open side of said housing and a close position to close said front open side of said housing;
a connection member connected between said door panel and said sliding plate for enabling said sliding plate to be moved with said door panel in and out of said housing;
a rack detachably and rotatably mounted at said sliding plate for holding toothbrushes and/or razors, said rack comprising an upper rack plate, a lower rack plate and a post holding said upper rack plate and said lower rack plate at different elevations, said upper rack plate comprising a plurality of insertion holes equiangularly spaced around said post for the insertion of toothbrushes and/or razors individually, said lower rack plate comprising a plurality of grooves corresponding to said insertion holes of said upper rack plate for the positioning of respective bottom ends of toothbrushes and/or razors that are respectively inserted through said insertion holes, said lower rack plate comprising a gearwheel integrated therein;

a motor fixedly mounted at said sliding plate and electrically connected to said control circuit;

a pinion meshed with said gearwheel of said lower rack plate and driven by said motor to rotate gearwheel of said lower rack plate and said rack relative to said sliding plate;

a control circuit mounted inside said housing;

a hot air generator mounted inside said housing and controllable by said control circuit to generate hot air;

an UV germicidal lamp mounted inside said housing and controllable by said control circuit to generate UV light;

a tact switch mounted at a front side of said housing and switchable to drive said control circuit to turn on said hot air generator and UV germicidal lamp for a predetermined length of time;

a power jack mounted outside said housing and electrically connected to said control circuit; and a power adapter adapted for electrically connecting said power jack to an external power source to provide electricity to said control circuit, said hot air generator and said UV germicidal lamp.

9. The toothbrush sterilization cabinet as claimed in claim 8, further comprising a motor housing fixedly mounted at said sliding plate to hold said motor therein.

10. The toothbrush sterilization cabinet as claimed in claim 8, wherein said control circuit is a programmable circuit programmed to turn off said hot air generator and said UV germicidal lamp a set time after said hot air generator and said UV germicidal lamp have been turned on.

* * * * *